United States Patent [19]
Rex

[11] Patent Number: 6,038,468
[45] Date of Patent: Mar. 14, 2000

[54] CATHETER LOCALISATION SYSTEM

[75] Inventor: James Alexander Rex, Hants, United Kingdom

[73] Assignee: Roke Manor Research Ltd., United Kingdom

[21] Appl. No.: 09/161,474

[22] Filed: Sep. 28, 1998

[30] Foreign Application Priority Data

Sep. 26, 1997 [GB] United Kingdom .................. 9720360

[51] Int. Cl.[7] ...................................................... A61B 5/05
[52] U.S. Cl. ............................................................ 600/424
[58] Field of Search .................................. 600/424, 407, 600/437; 128/916

[56] References Cited

U.S. PATENT DOCUMENTS

| | | | |
|---|---|---|---|
| 4,794,931 | 1/1989 | Yock ................................... | 128/660.03 |
| 4,878,500 | 11/1989 | Ophir et al. ........................ | 128/660.01 |
| 5,447,154 | 9/1995 | Cinquin et al. ...................... | 128/653.1 |
| 5,480,422 | 1/1996 | Ben-Haim .............................. | 607/122 |
| 5,497,776 | 3/1996 | Yamazaki et al. .................. | 128/660.09 |
| 5,588,432 | 12/1996 | Crowley .............................. | 128/660.93 |
| 5,727,552 | 3/1998 | Ryan ..................................... | 128/653.1 |
| 5,954,649 | 9/1999 | Chia et al. .............................. | 600/424 |

FOREIGN PATENT DOCUMENTS

| | | |
|---|---|---|
| WO 89/04142 | 5/1989 | European Pat. Off. . |
| 2279743A | 1/1995 | United Kingdom . |

*Primary Examiner*—Marvin M. Lateef
*Assistant Examiner*—Eleni Mantis Mercader
*Attorney, Agent, or Firm*—Evenson, McKeown, Edwards & Lenahan, P.L.L.C.

[57] ABSTRACT

A catheter localization system for determining a position of a catheter (1, 2) within a part of the human or animal body (3), comprising at least one catheter (1, 2) having a plurality of acoustic transducers (6) disposed on the catheter in a spaced apart relationship. Each acoustic transducer (6) is arranged to transmit or receive acoustic signals (12, 14). A signal processing unit (8) is coupled to the plurality of acoustic transducers (6) and arranged to selectively energize the transducers (6) and consequent upon acoustic signals (12, 14) received by the acoustic transducers (6) generate a plurality of acoustic transfer functions (24, 28) representative of an effect of the part of the body on the acoustic signals, which signal processing unit (8) further operates to generate data appertaining to a three dimensional representation (36) of the part (4) of the human body (3) in accordance with the plurality of transfer functions.

18 Claims, 3 Drawing Sheets

CATHETER LOCALISATION SYSTEM

The present invention relates to catheter localisation systems which operate to determine a position of a head of a catheter with reference to a part of the human or animal body.

Catheters provide a means for accessing a remotely located part of the human or animal body via a vein or artery so as to provide a means to perform medical diagnostics or treatment of that part of the body. The term catheter as used herein therefore includes any medical tool which serves to provide remote access to a part of a human or animal body via a convenient conduit such as a vein by a substantially invasive surgical technique. The term includes endoscopes and similar tools for remote access of the body.

A catheter may be provided with an electric sensor disposed on a tip of the catheter which may further comprise an elongated flexible member arranged to move axially within an outer sheath. The tip including the electric sensor may be disposed and arranged to pass through a vein or artery. By moving the elongated flexible member within the vein or artery positioning of the tip of the catheter at or near a part of the body is facilitated. The sensor thereafter provides signals representative of electrical activity of the part of the body. In such operations it is an important requirement to be able to determine a position of the catheter tip so as to provide correct interpretation of the diagnostic information and correct positioning of the catheter during treatment. A process wherein the position of the catheter tip is determined with reference to the part of the body being treated is known as localisation.

Electrocardiography is a process for recording electrical signals created by the heart using electrodes applied externally and more particularly electrodes positioned on tips of catheters inserted within the heart. In known endocardial catheter technology, great use is made of in-theatre fluoroscopy to locate and guide catheters to positions within the heart where measurements are required. The use of fluoroscopy has a disadvantage in that inevitably theatre staff and patients are exposed to X-ray radiation. In known catheter localisation systems, a reference catheter is used to provide a predetermined position at a known location inserted into the body under guidance of X-ray fluoroscopy. The X-ray fluoroscopy is used to facilitate positioning of the reference catheter at a predetermined position throughout the procedure in a convenient and anatomically well defined position such as a coronary sinus. The reference catheter serves to provide to a certain level, some compensation for the movement caused by the patient's breathing and the beat of the heart. This is effected, as a result of movement of both reference and measurement catheters being substantially the same for both catheters. Having regard to known catheters and catheter tracking systems, improving the direction and location of catheters to desired positions represents a technical problem, which is addressed by the catheter localisation system according to claim 1, and method according to claim 9.

According to the present invention there is provided a catheter localisation system for determining a position of a catheter within a part of the human or animal body, said catheter localisation system comprising at least one catheter having a plurality of acoustic transducers disposed on said at least one catheter in a spaced apart relationship, each of which acoustic transducers is arranged to transmit or receive acoustic signals and a signal processing unit coupled to said plurality of acoustic transducers and arranged to selectively energise said transducers and consequent upon acoustic signals received by said acoustic transducers generate a plurality of acoustic transfer functions representative of an effect of said part of said body on said acoustic signals, which signal processing unit further operates to generate data appertaining to a three dimensional representation of said part of the human body in accordance with said plurality of transfer functions.

By arranging for at least one of the acoustic transducers to generate a known acoustic signal and by determining and measuring reflections of the acoustic signal from the wall of the part of the body in which the catheter head is disposed, an acoustic transfer function may be determined for each acoustic signal generated by one of the acoustic transducers and received by another of the acoustic transducers, or by the same transducer.

Advantageously the signal processing unit will operate to synthesise a model of the part of the human body and consequent upon said plurality of acoustic transfer functions generated from acoustic signals received by said acoustic transducers operate to adapt said model so as to provide a substantially close fit between the acoustic transfer functions and said synthesised model of the part of the body.

By arranging for a signal processing unit to correlate the acoustic transfer functions with an estimated model of a surface wall of the part of the human body, and providing an iterative process of fitting this model to said plurality of acoustic transfer functions, the signal processing unit will serve to generate a three dimensional map of the inside of the part of the human or animal body. From known or subsequently generated distance measurements, a position of the acoustic transducers along the catheter may be determined, thereby providing in combination with the three dimensional map information appertaining to a position of the catheter within the body part. The catheter position may therefore be determined with a substantial reduction in an amount of X-ray fluoroscopy.

Advantageously the acoustic signals generated by said acoustic transducers may be modulated so as to provide contemporaneous detection of said acoustic signals. This provides substantially contemporaneous generation of said acoustic transfer functions, from which said three dimensional map of said body part may be generated, independently of any movement of said body part.

According to a first aspect of the present invention there is provided a method of determining a position of a catheter with reference to a three dimensional map of a part of a human or animal body, comprising the steps of, generating at least one acoustic signal from acoustic transducers acting as acoustic signal sources within the part of the human or animal body detecting acoustic signals reflected via walls of the part of the body, with a plurality of acoustic signal detectors, determining a plurality of acoustic transfer functions corresponding to the detected acoustic signals by correlating said detected signals with said generated acoustic signal synthesising a three dimensional model of the part of the human or animal body, and adjusting the model of the human or animal body in accordance with the acoustic transfer functions so that a three dimensional model of the part of the human or animal body is synthesised, from which information as to the location of the catheter head may be determined.

One embodiment of the present invention will now be described by way of example only with reference to the accompanying drawings wherein

DETAILED DESCRIPTION OF THE PREFERRED EMBODIMENTS

Figure 1:
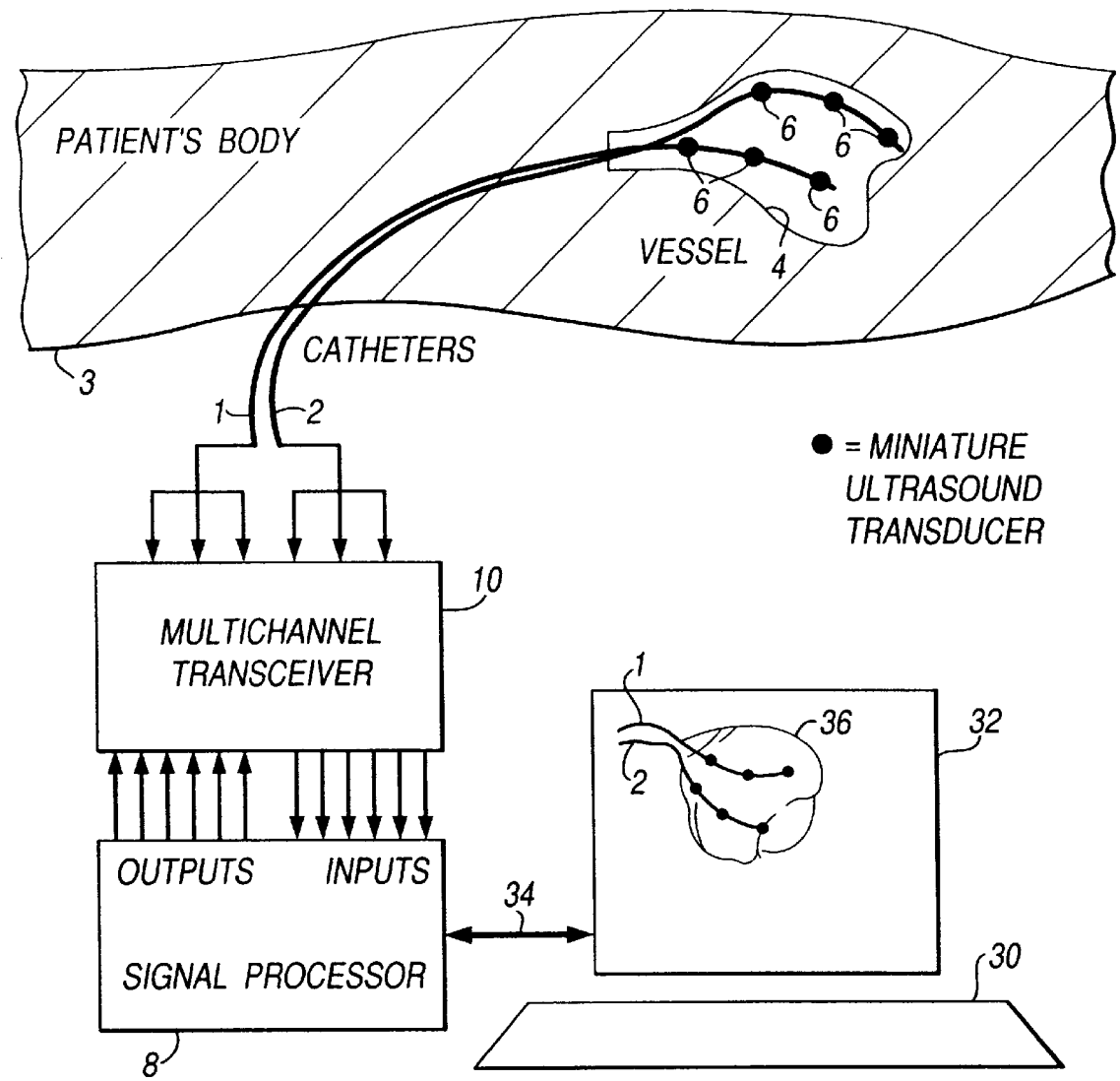
FIG. 1 is an illustrative block diagram of a catheter localisation system.

A catheter localisation system in accordance with one embodiment of the present invention is presented in FIG. 1. In FIG. 1 two catheters 1, 2, are shown to be inserted into a patient's body 3 and to be extended into the heart of the patient. Although the illustrative embodiment shown in FIG. 1 is provided with two catheters 1, 2, it will be readily appreciated that other embodiments may be arranged such that acoustic transducers 6 disposed on the catheters 1 and 2 may be disposed on a single catheter so that the catheter tracking arrangement can be effected with reference to one catheter only.

The catheters 1 and 2 are coupled to a signal processing unit 8 via a multi-channel transceiver 10. The signal processing unit 8 operates to excite the acoustic transducers selectively such that by either temporarily or phase modulating acoustic signals generated by each of the acoustic transducers 6, acoustic signals from any one of the acoustic transducers 6 may be uniquely identified. Acoustic signals generated by one of the acoustic transducers 6 are thereafter detected by others of the acoustic transducers 6 and for each acoustic signal generated and for each acoustic transducer receiving this acoustic signal, an acoustic transfer function may be determined as will shortly be described. Signals representative of the acoustic signals detected by each of the acoustic transducers 6 are fed to the signal processor via the multi-channel transceiver 10. The multi-channel transceiver 10 serves to provide separation and determination of signals representative of detected acoustic signals from each of the acoustic transducers 6. The multi-channel transceiver 10, thereby serves to provide a facility through which acoustic transducers may be selectively excited and signals detected thereby may be selectively fed to the signal processing unit 8.

Figure 2:
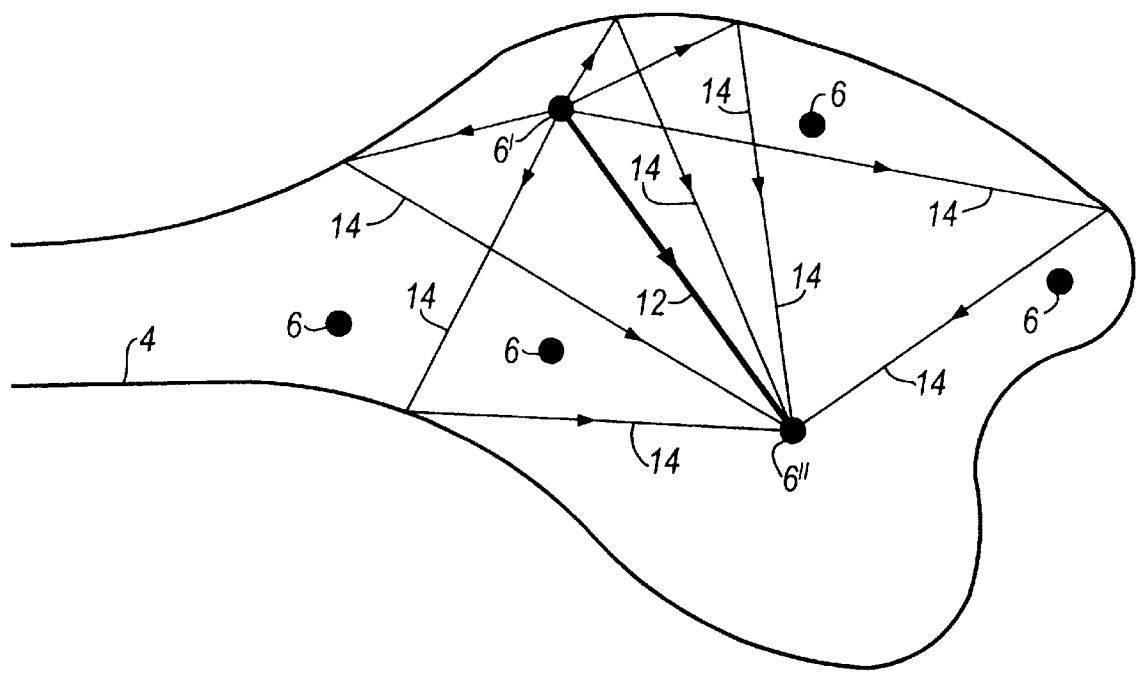
FIG. 2 is a schematic diagram representing the generation of an acoustic transfer function from scattered and reflected acoustic signals.
Figure 3:
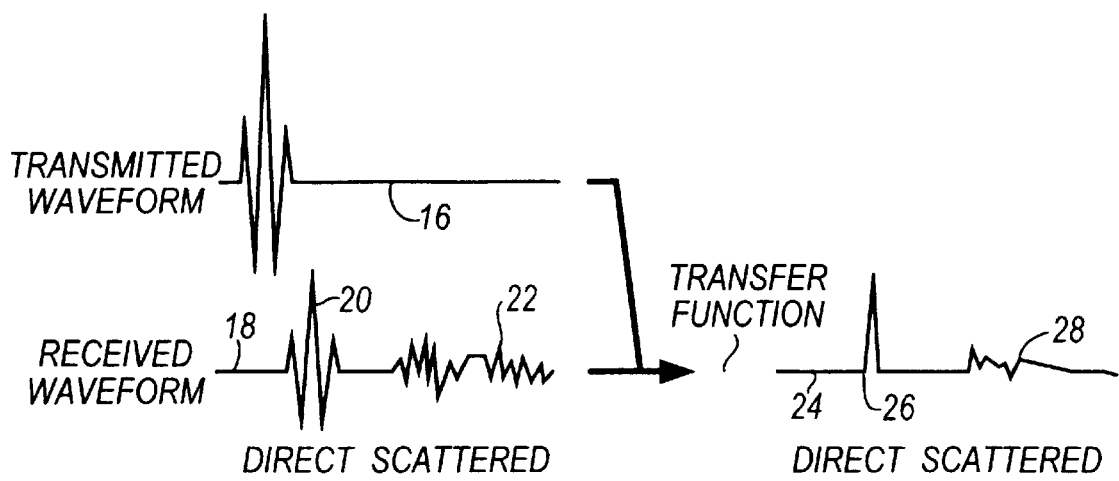
FIG. 3 is a set of three waveform diagrams providing an illustration of the generation of the acoustic transfer function.

The signal processing unit 8, operates to determine a three dimensional map of the part of the human body 4 in which the catheters 1 and 2 are disposed. Generation of the three dimensional map will now be described with reference to FIGS. 2 and 3 where parts also appearing in FIG. 1 bear identical numerical designations. In FIG. 2 acoustic transducers 6 associated with the catheters 1 and 2 are shown to be disposed within the heart 4. One of the transducers 6' is shown to generate an acoustic signal which is thereafter received by another of the acoustic transducers 6". The acoustic signal is received along a direct path 12 and along a plurality of indirect paths 14 which indirect paths represent paths taken by the acoustic signals reflected via the heart wall 4. The diagram shows only some of many indirect paths. Acoustic signals received by the receiver acoustic transducer 6" are illustrated in FIG. 3. In FIG. 3 the acoustic signal generated by the acoustic transducer 6' is shown as waveform signal 16. The signal representative of the acoustic signals received by the receiving acoustic transducer 6" is shown as waveform 18. The waveform 18 is shown to be comprised of a signal from the direct path 12 and a signal from the indirect paths 14 which are designated waveform 20 and 22. The waveform 22 is shown to be comprised of a plurality of scattered signals which are formed from reflections of the acoustic signal from the heart wall. For each of the acoustic transducers receiving acoustic signals generated by the acoustic transducer 6', the signal processing unit 8 operates to generate an acoustic transfer function. In FIG. 3 an acoustic transfer function generated for the received waveform 18 in accordance with the transmitted waveform 16 is shown to be illustrated by a signal waveform diagram 24. By correlating the transmitted acoustic signal with the acoustic signals received at the receiving acoustic transducer 6", the acoustic transfer function 24 is generated. This is again shown to be comprised of a direct component 26 and a scattered component 28.

After generating a plurality of acoustic transfer functions from the acoustic transducers disposed within the vessel 4, the signal processing unit operates to generate a three dimensional map of the inside of the heart wall 4 from which a location of the catheters 1 and 2 may be determined. This is achieved by generating a three dimensional synthesised model of the inside of the heart wall 4 and iteratively adapting this model to fit the acoustic transfer functions measured by the acoustic transducers. In the catheter localisation system shown in FIG. 1 the signal processing unit 8, operates to generate the shape of the heart wall since the heart wall will be a strongly reflecting feature which can be modelled as a surface surrounding the acoustic transducers. The surface shape is then adjusted to match the calculated reflections in accordance with a best fit image of the heart wall corresponding to the plurality of acoustic transfer functions generated. This is known as a holographic imaging technique. The accuracy of the holographic imaging technique is increased by employing a more detailed model of the image and by making more observations of wave scattering in the region. The greater the distances between the transducers from which acoustic transfer functions are generated, the more accurate the three dimensional map of the inside of the heart wall will be. Hence, the acoustic transducers can be spaced apart accordingly along the length of the catheter. To effect the holographic imaging, it is necessary that the relative positions of all the acoustic transducers along the catheter head are known. However, in a case where the transducers are mounted on a flexible catheter the position of the acoustic transducers may move with respect to each other. This means that the relative positions of the acoustic transducers 8, must be continually measured as the catheters move. One way to effect this operation is to measure a direct unscattered sound transmission between transducers. A distance between two acoustic transducers is equal to the product of the time taken for the acoustic signal to travel between one to the other acoustic sensor and the average speed of the acoustic signals in the medium between them. A direct sound propagation time between a pair of acoustic transducers can be determined at the same time as the scattered sound. The average sound speed can thereafter be estimated from the material through which the acoustic signals have passed. Thus distances between pairs of acoustic transducers may be determined in accordance with this method which is known as sonomicrometry. By determining the distances between several pairs of acoustic transducers, the relative positions of all of them may be determined.

In the catheter localisation system as hereinbefore described it is advantageous that the acoustic transducers are miniature and are capable of transmitting and receiving acoustic signals substantially omnidirectionally. Although the embodiment of the invention has been shown with acoustic transducers disposed on two separate catheters, it will be readily appreciated that the acoustic transducers could be disposed at different sites on a signal catheter.

Figure 4:
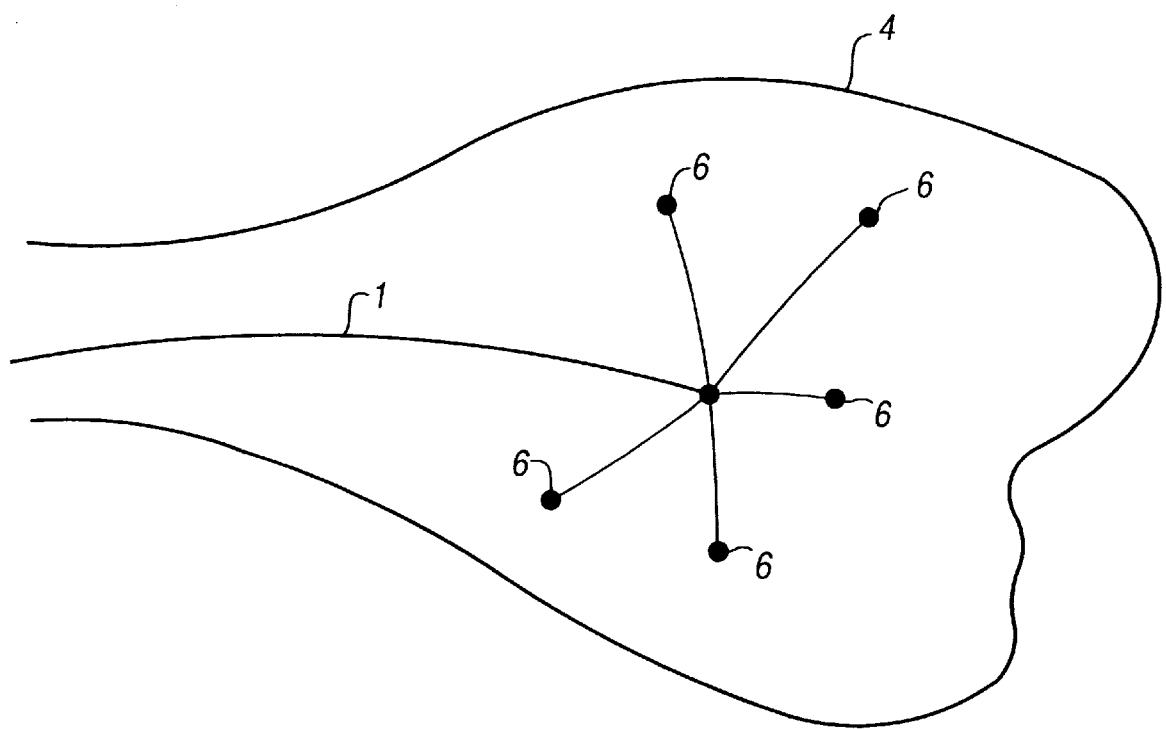
FIG. 4 is an illustrative schematic diagram of a catheter with extensible arms deployed in a patient's heart.

In yet a further embodiment acoustic transducers may be mounted on extensible arms or similar structures and arranged to mechanically extend and spread the position of the acoustic transducers apart once the catheter head is disposed inside the part of the body which is to be investigated. This is illustrated in FIG. 4, where catheter 1 is shown to have arms 38, deployed with acoustic transducers 6 disposed on a distal end thereof.

An image of anatomical structures in a region in the vicinity of the acoustic transducers is synthesised from the acoustic transfer functions measured. This may be achieved using a computer with an associated user interface which is coupled to the signal processing unit 8, which serves to display images determined by the signal processing unit, and to accept commands to adjust system parameters. As will be appreciated by those skilled in the art, the images displayed on the computer may include indications of position of the catheter mounted transducers and will therefore provide a means for guiding the catheters relative to the surrounding anatomy. This is shown in FIG. 1 with the computer 30 and display monitor 32 coupled to the signal processor via interface 34.

As aforementioned, the three dimensional map of the structure of the part of the body being investigated is synthesised from the acoustic transfer functions measured by the acoustic transducers. This is illustrated in FIG. 1 by a three dimensional synthesised model 36, shown on the computer display 32. This may be effected using a software model of the anatomical structures which surround the acoustic transducers. Such a model can assume a wide range of anatomical structures and can predict the acoustic transfer function between two acoustic transducers or correspondingly the self transfer function between a single transducer and itself. For each measured acoustic transfer function a corresponding prediction is made using an initial estimate of the anatomy. Each predicted acoustic transfer function is compared with its measured acoustic transfer function and the degree of overall fit between the predictions and the measured transfer functions is assessed. Hence the model of the anatomy is then correspondingly adjusted and new predictions are made and compared with the transfer functions measured. This process is iteratively repeated until an overall best fit between predicted acoustic transfer functions and measured acoustic transfer functions is effected. Hence the model of the anatomy which provides a best fit is then displayed on the computer display 32, as shown. Relative positions of the acoustic transducers may be determined along with the shape of the anatomy.

As will be readily appreciated by those skilled in the art, various modifications may be made to the embodiments hereinbefore described without departing from the scope of the present invention. In particular the acoustic transducers may be ultra sound transducers and the acoustic signals may be ultra sound signals. Furthermore the acoustic transducers may be disposed on any part of the catheter including the elongated member.

I claim:

1. A catheter localisation system for determining a position of a catheter within a part of the human or animal body, said catheter localisation system comprising at least one catheter having a plurality of acoustic transducers disposed on said at least one catheter in a spaced apart relationship, each of which acoustic transducers is arranged to transmit or receive acoustic signals and a signal processing unit coupled to said plurality of acoustic transducers and arranged to selectively energise said transducers and consequent upon acoustic signals received by said acoustic transducers generate a plurality of acoustic transfer functions representative of an effect of said part of said body on said acoustic signals, which signal processing unit further operates to generate data appertaining to a three dimensional map of said part of the body in accordance with said plurality of transfer functions.

2. A catheter localisation system as claimed in claim 1, wherein said signal processing unit operates to synthesise a model of the part of the body and consequent upon said plurality of acoustic transfer functions generated from acoustic signals received by said acoustic transducers operates to adapt said model so as to provide a substantially close fit between the acoustic transfer functions and said synthesised model of the part of the body, said adapted synthesised model being said three dimensional map.

3. A catheter localisation system as claimed in claim 2, wherein said signal processing unit operates to calculate relative positions of the acoustic transducers from times of flight of acoustic signals between a plurality of pairs of acoustic transducers calculated from said plurality of acoustic transfer functions, thereby facilitating adaptation of said synthesised model of said body part.

4. A catheter localisation system as claimed in claim 2, wherein said signal processing unit further operates to determine a position of said catheter in said body part from said three dimensional map of said body part in combination with said relative positions of the acoustic transducers and known data appertaining to a position of said acoustic transducers on said catheter.

5. A catheter localisation system as claimed in claim 1, wherein said signal processing unit operates to calculate relative positions of the acoustic transducers from times of flight of acoustic signals between a plurality of pairs of acoustic transducers calculated from said plurality of acoustic transfer functions, thereby facilitating adaptation of said synthesised model of said body part.

6. A catheter localisation system as claimed claim 5, wherein said signal processing unit further operates to determine a position of said catheter in said body part from said three dimensional map of said body part in combination with said relative positions of the acoustic transducers and known data appertaining to a position of said acoustic transducers on said catheter.

7. A catheter localisation system as claimed in claim 5, wherein said signal processing unit further operates to determine a position of said catheter in said body part from said three dimensional map of said body part in combination with said relative positions of the acoustic transducers and known data appertaining to a position of said acoustic transducers on said catheter.

8. A catheter localisation system as claimed in claim 1, wherein said signal processing unit in combination with acoustic transducers is arranged to modulate said acoustic signals so as to provide contemporaneous detection of said acoustic signals and substantially contemporaneous generation of said acoustic transfer functions, from which said three dimensional map of said body part may be generated in a time which substantially obviates effects of any movement of said body part.

9. A catheter localisation system as claimed in claim 1, further including a transceiver coupled to said catheter and said signal processing unit and arranged in operation to multiplex signals communicated between said signal processing unit and said plurality of acoustic transducers, thereby separating signals communicated to each acoustic transducer.

10. A catheter localisation system as claimed in claim 1, further including a user interface including a display means on which said three dimensional map of said body part and said position of said catheter may be displayed.

11. A catheter localisation system as claimed in claim 1, wherein said catheter has a plurality of extensible arms upon which said acoustic transducers are mounted at distal ends thereof, which arms may be deployed when said catheter is disposed in said body part, thereby providing substantially improved spatial separation of said plurality of acoustic transducers.

12. A method of determining a position of a catheter with reference to a three dimensional model of a part of a human or animal body, comprising the steps of, generating at least one acoustic signal from acoustic transducers acting as acoustic signal sources within the part of the body, detecting acoustic signals reflected via walls or the other features of the part of the body, with a plurality of acoustic signal detectors, determining a plurality of acoustic transfer functions corresponding to the detected acoustic signals by correlating said detected signals with said generated acoustic signal, synthesising a three dimensional model of the part of the body, and adjusting the three dimensional model of the human or animal body in accordance with the acoustic transfer functions so that a three dimensional model of the part of the body is synthesised, from which information as to the location of the catheter head may be determined.

13. A method of determining a position of a catheter as claimed in claim 12, further including the step of, calculating relative positions of the acoustic transducers along said catheter from times of flight of acoustic signals between a plurality of pairs of acoustic transducers calculated from said plurality of acoustic transfer functions, thereby facilitating adaptation of said synthesised model of said body part.

14. A method of determining a position of a catheter as claimed in claim 13, further including the step of, determining a position of said catheter in said body part from said three dimensional model of said body part in combination with said relative positions of the acoustic transducers and known data appertaining to a position of said acoustic transducers on said catheter.

15. A method of determining a position of a catheter as claimed in claim 13, further including the step of, modulating said acoustic signals so as to facilitate contemporaneous detection of said acoustic transfer functions.

16. A method of determining a position of a catheter as claimed in claim 12, further including the step of, determining a position of said catheter in said body part from said three dimensional model of said body part in combination with said relative positions of the acoustic transducers and said known data appertaining to a position of said acoustic transducers on said catheter.

17. A method of determining a position of a catheter as claimed in claim 16, further including the step of, modulating said acoustic signals so as to facilitate contemporaneous detection of said acoustic transfer functions.

18. A method of determining a position of a catheter as claimed in claim 12, further including the step of, modulating said acoustic signals so as to facilitate contemporaneous detection of said acoustic transfer functions.

\* \* \* \* \*